United States Patent
Zalutsky et al.

(10) Patent No.: US 9,839,704 B2
(45) Date of Patent: Dec. 12, 2017

(54) PROSTHETIC COMPOUNDS FOR LABELING INTERNALIZING BIOMOLECULES

(71) Applicant: Duke University, Durham, NC (US)

(72) Inventors: Michael Zalutsky, Chapel Hill, NC (US); Ganesan Vaidyanathan, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/888,480

(22) PCT Filed: May 2, 2014

(86) PCT No.: PCT/US2014/036615
§ 371 (c)(1),
(2) Date: Nov. 2, 2015

(87) PCT Pub. No.: WO2014/179715
PCT Pub. Date: Nov. 6, 2014

(65) Prior Publication Data
US 2016/0074541 A1    Mar. 17, 2016

Related U.S. Application Data

(60) Provisional application No. 61/818,722, filed on May 2, 2013.

(51) Int. Cl.
| | | |
|---|---|---|
| A61K 51/10 | (2006.01) | |
| C07D 403/12 | (2006.01) | |
| C07D 207/46 | (2006.01) | |
| C07D 207/416 | (2006.01) | |
| C07D 487/04 | (2006.01) | |
| C07B 59/00 | (2006.01) | |
| A61K 51/08 | (2006.01) | |

(52) U.S. Cl.
CPC ........ *A61K 51/1093* (2013.01); *A61K 51/088* (2013.01); *A61K 51/1051* (2013.01); *C07B 59/002* (2013.01); *C07D 207/416* (2013.01); *C07D 207/46* (2013.01); *C07D 403/12* (2013.01); *C07D 487/04* (2013.01)

(58) Field of Classification Search
CPC .... A61K 51/10; C07D 403/12; C07D 207/46; C07D 207/416; C07D 487/04; C07B 59/00
See application file for complete search history.

(56) References Cited

U.S. PATENT DOCUMENTS

| 2007/0031333 A1 | 2/2007 | Mease et al. |
| 2007/0276231 A1 | 11/2007 | Low et al. |
| 2013/0052132 A1 | 2/2013 | Saji et al. |

FOREIGN PATENT DOCUMENTS

| WO | 2009080561 A1 | 7/2009 |
| WO | 2010033196 A2 | 3/2010 |

OTHER PUBLICATIONS

Hendricks et al., 2012, caplus an 2012:502903.*
Shuanglong Liu et al., "Lewis Acid-Assisted Isotopic 18 F-19 F Exchange in BODIPY Dyes: Facile Generation of Positron Emission Tomography/Fluorescence Dual Modality Agents for Tumor Imaging", Theranostics, vol. 3, No. 3, pp. 181-189, Jan. 1, 2013.
Vaidyanathan, Ganesan, and Michael R. Zalutsky. "Synthesis of N-succinimidyl 4-guanidinomethyl-3-[I] iodobenzoate: a radioiodination agent for labeling internalizing proteins and peptides." Nature protocols 2.2 (2007): 282-286.
Rojas, Santiago, et al. "Efficient cysteine labelling of peptides with N-succinimidyl 4-[18 F] fluorobenzoate: stability study and in vivo biodistribution in rats by positron emission tomography (PET)." RSC Advances 3.21 (2013): 8028-8036.
International Search Report—PCT/US2014/036615—dated Sep. 3, 2014.

* cited by examiner

*Primary Examiner* — Sun Jae Yoo
(74) *Attorney, Agent, or Firm* — Banner & Witcoff, Ltd.

(57) ABSTRACT

Prosthetic compounds are disclosed that are effective for radiolabeling biomolecules with 18F. Representative biomolecules include antibodies (e.g., monoclonal antibodies (mAbs) and nanobodies (sdAbs)), antibody fragments, and peptides that may have an affinity for particular types of cells, such as cancer cells. The prosthetic compounds effectively address the art-recognized difficulties associated with the retention of radioactivity within the targeted cells, due to internalization of the biomolecule, followed by proteolytic degradation. Representative prosthetic compounds include (i) a succinimidyloxycarbonyl moiety, (ii) a radioactive moiety bearing 18F, and (iii) a charged moiety, i.e., a moiety that is charged under the physiological conditions of the internal cell environment.

19 Claims, 10 Drawing Sheets

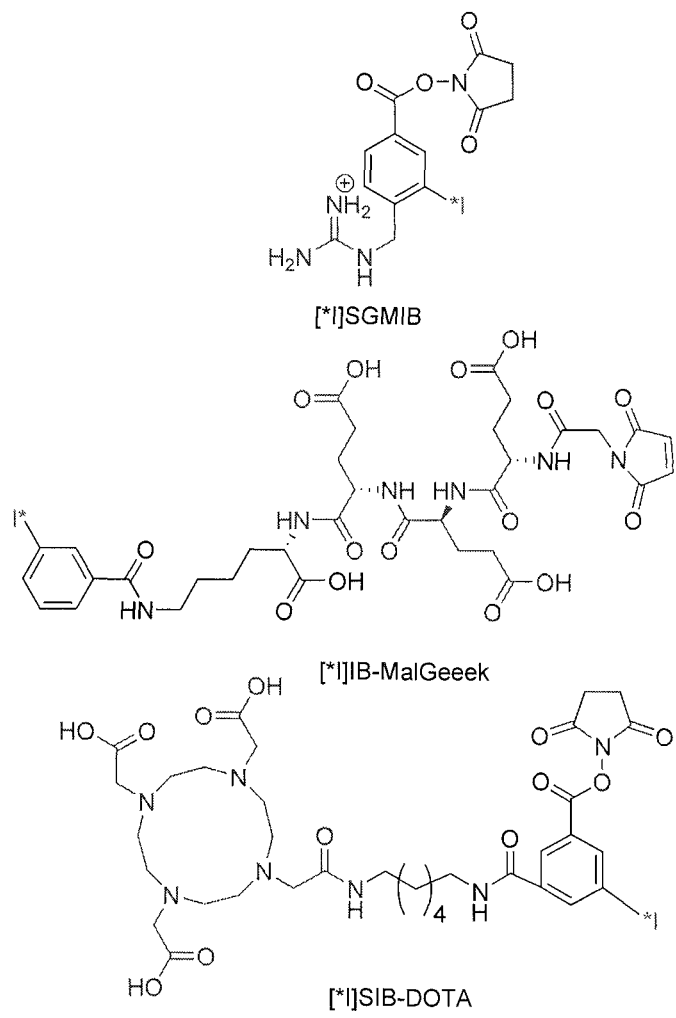
Figure 1. Structure of [*I]SGMIB, [*I]IB-MalGeeek, and [*I]SIB-DOTA

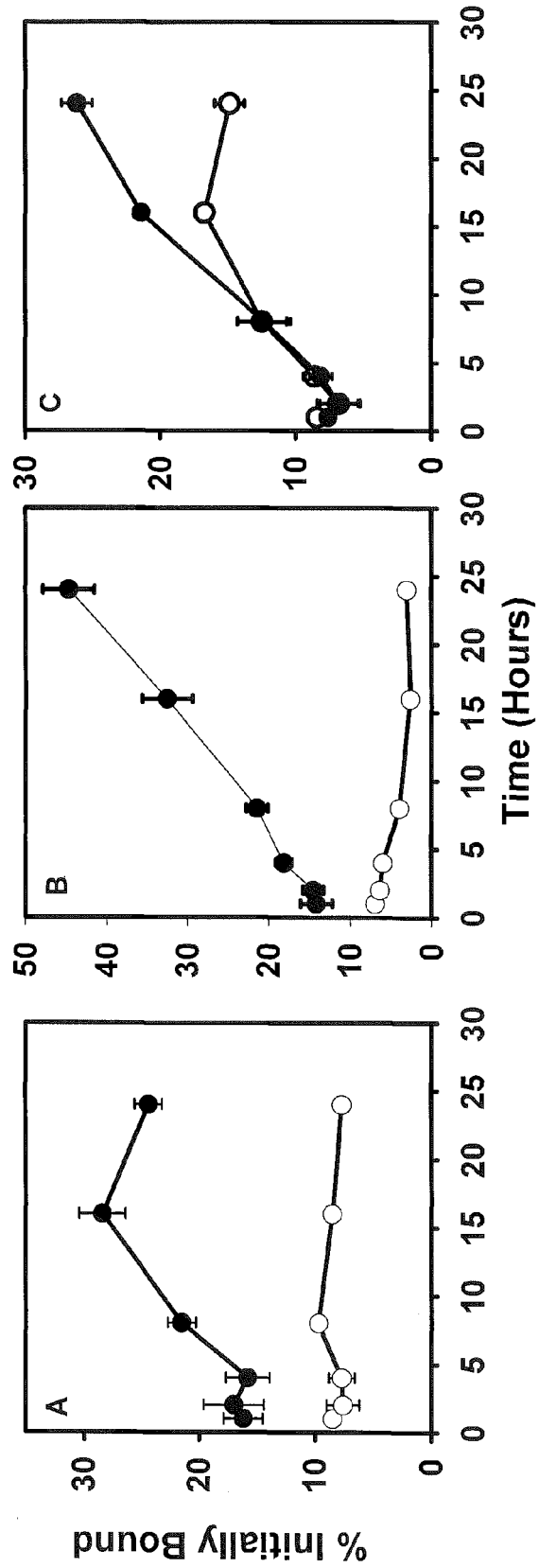

Figure 2. Intracellular radioactivity over time from paired-label internalization of anti-EGFRvIII antibody L8A4 labeled with various methods by EGFRvIII-expressing Glioma cells. A) [$^{131}$I]SGMIB (closed circle) versus directly labeled with $^{125}$I (open circle). B) [$^{131}$I]IB-MalGeeek (closed circle) versus directly labeled with $^{125}$I (open circle). C) [$^{131}$I]SIB-DOTA (closed circle) vs [$^{125}$I]SGMIB (open circle)

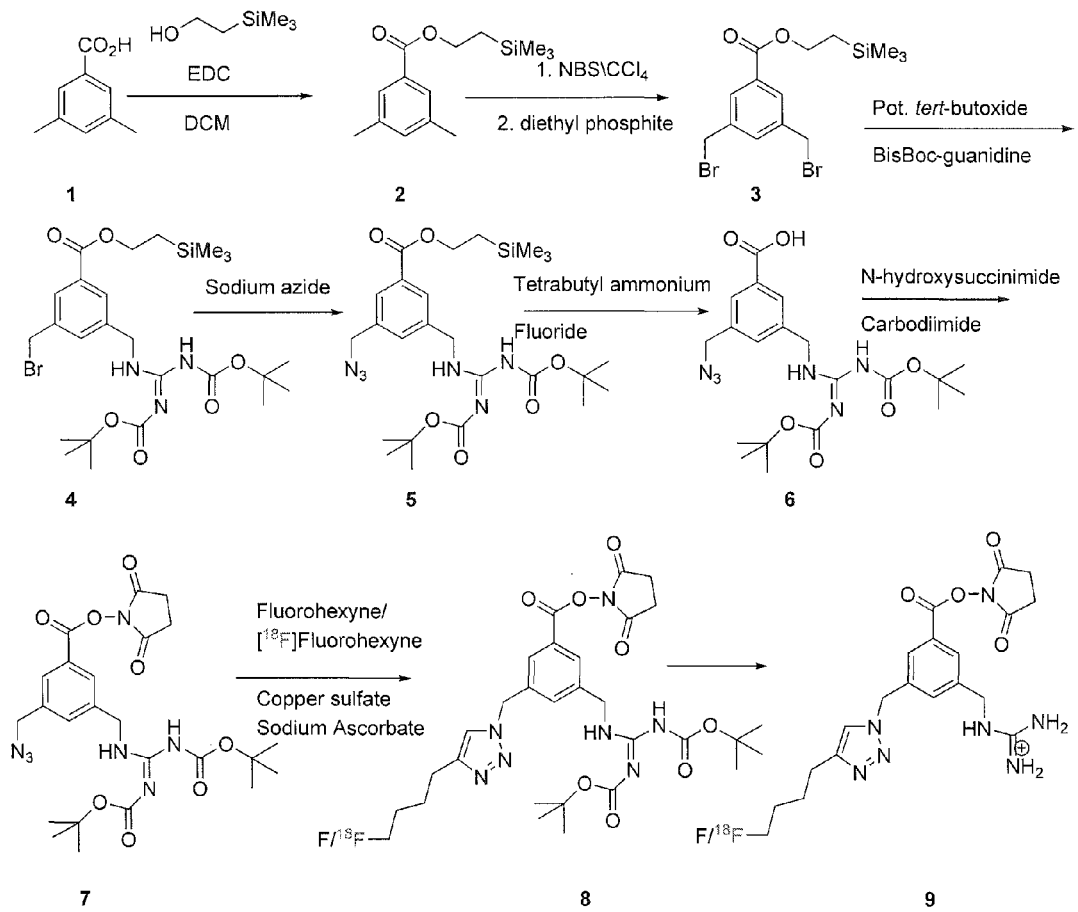
Figure 3. Scheme for the synthesis of azide precursor, standard and ¹⁸F-labeled SFBTMGMB Desired reaction-step 1
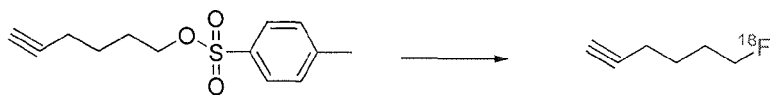
Potential side reactions- step 1
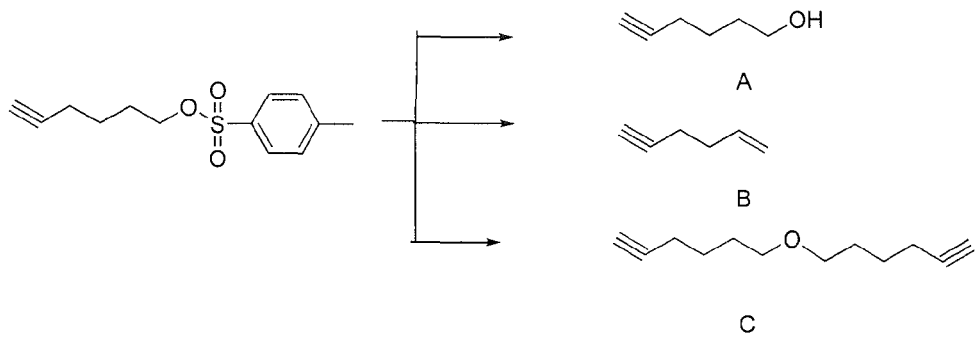
Desired reaction- step 2
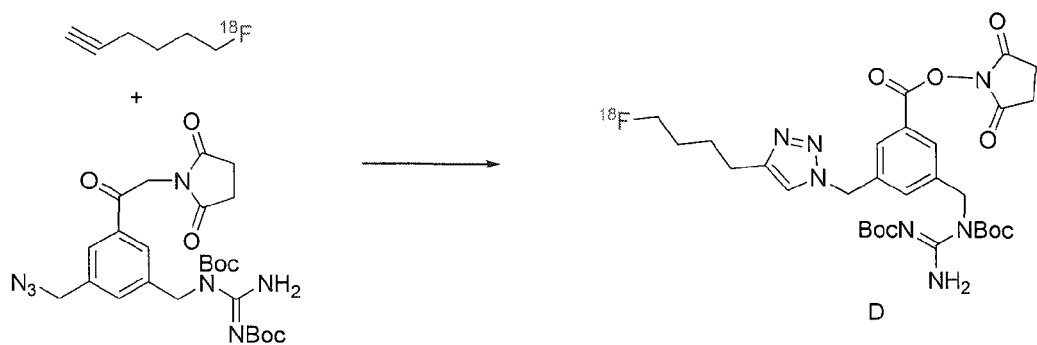
Side reaction-step 2
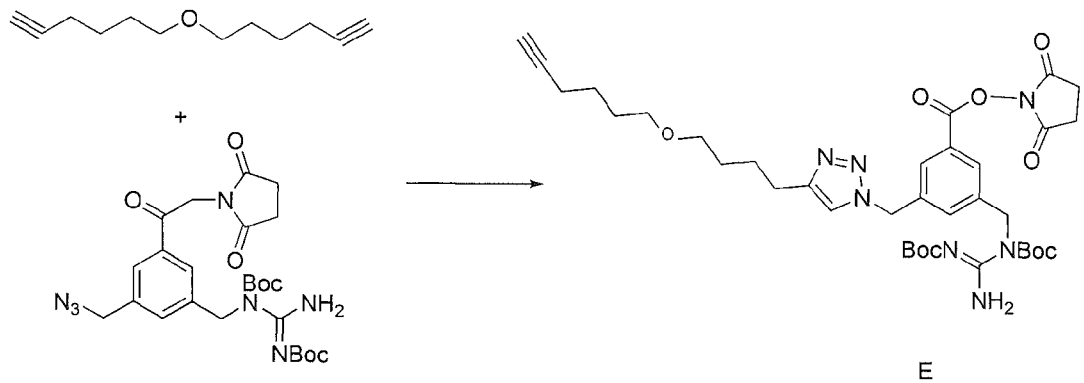
Figure 4. Potential side reaction leading up to the formation of side product E

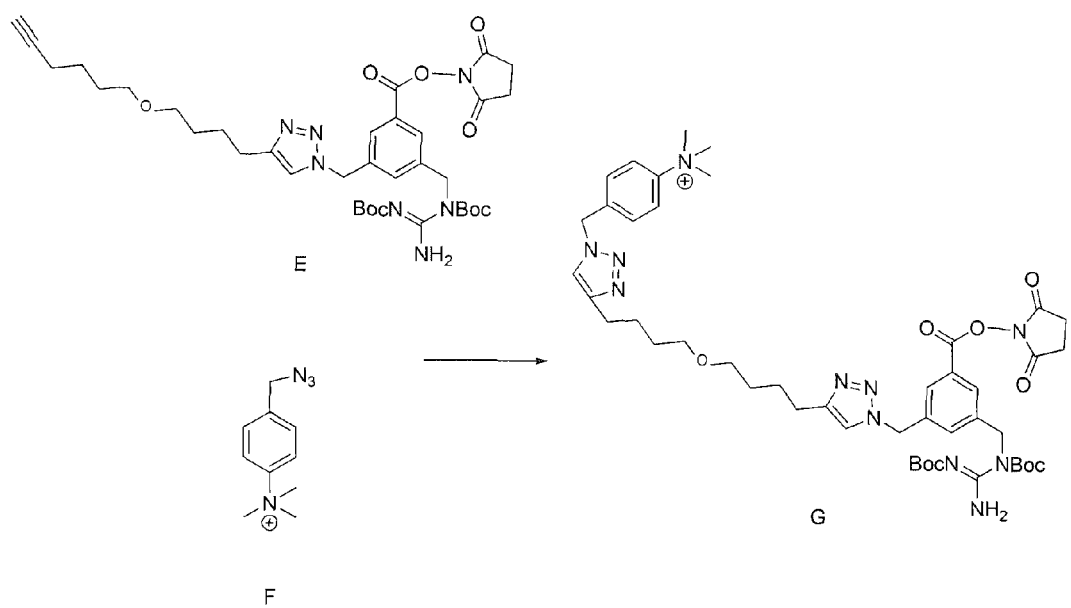
Figure 5. Approach to scavenge the side product.

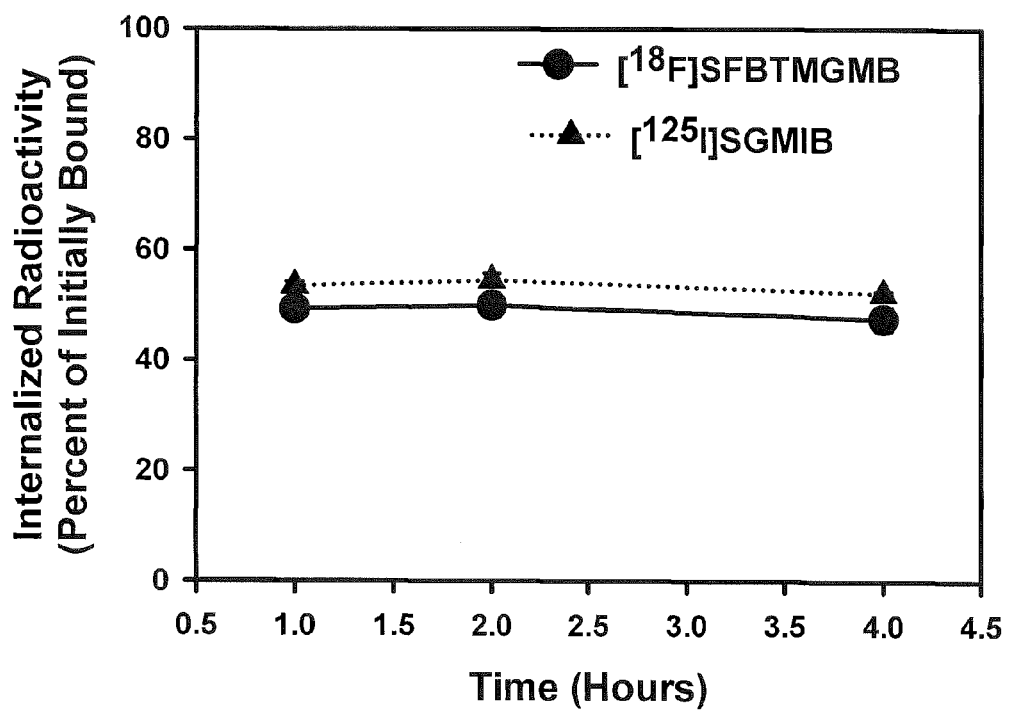
Figure 6. Paired-label internalization of 5F7 nanobody labeled using [$^{125}$I]SGMIB and [$^{18}$F]SFBTMGMB in BT 474M1 breast cancer cells.

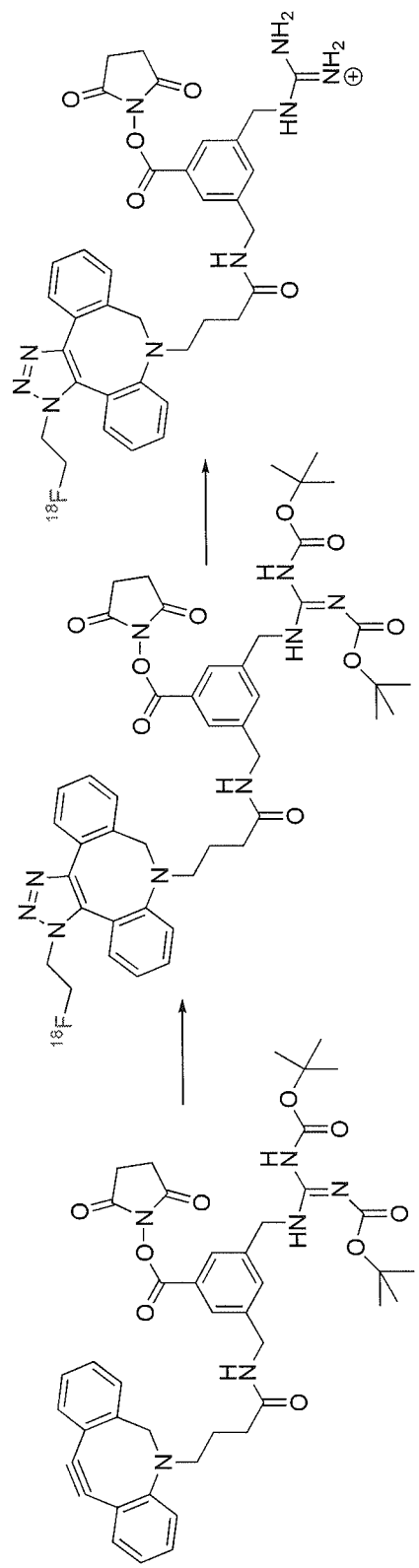
Figure 7. Residualizing agent that can be derived from copper-free click reaction

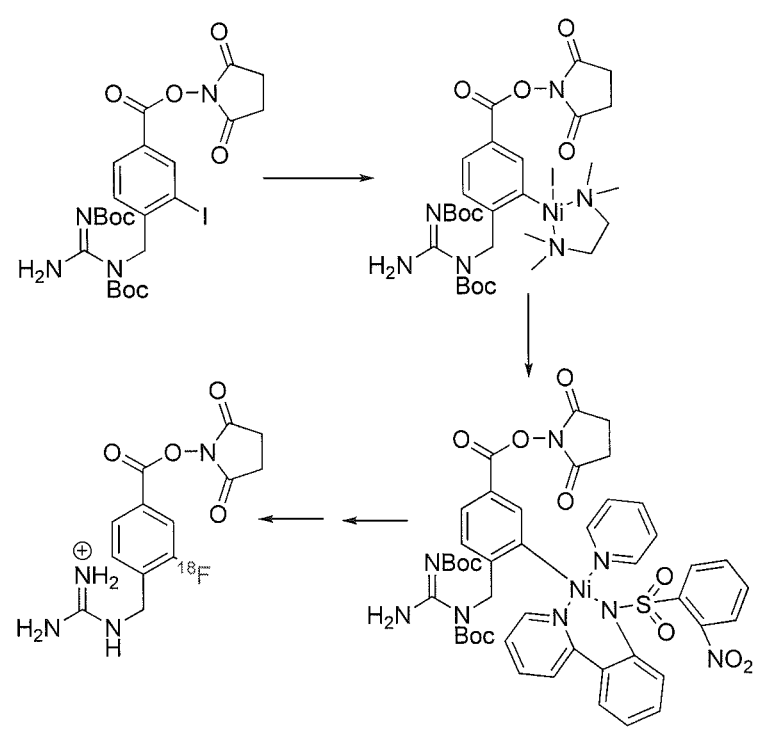
Figure 8. Approach to synthesizing [18F]SFGMB using Nickel Chemsitry

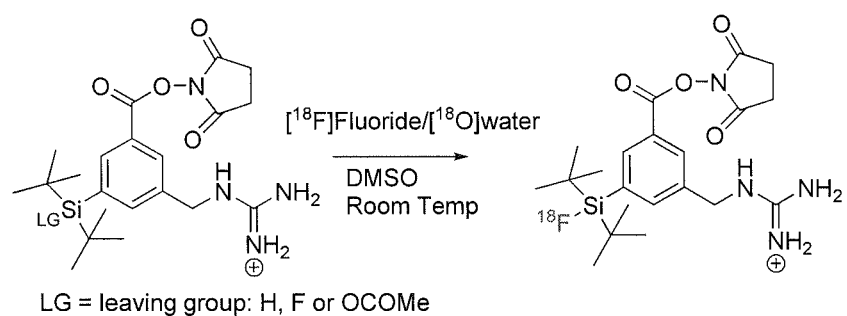
LG = leaving group: H, F or OCOMe
Figure 9. Synthesis of $^{18}$F-labeled SGMIB analogue by the SiFA approach

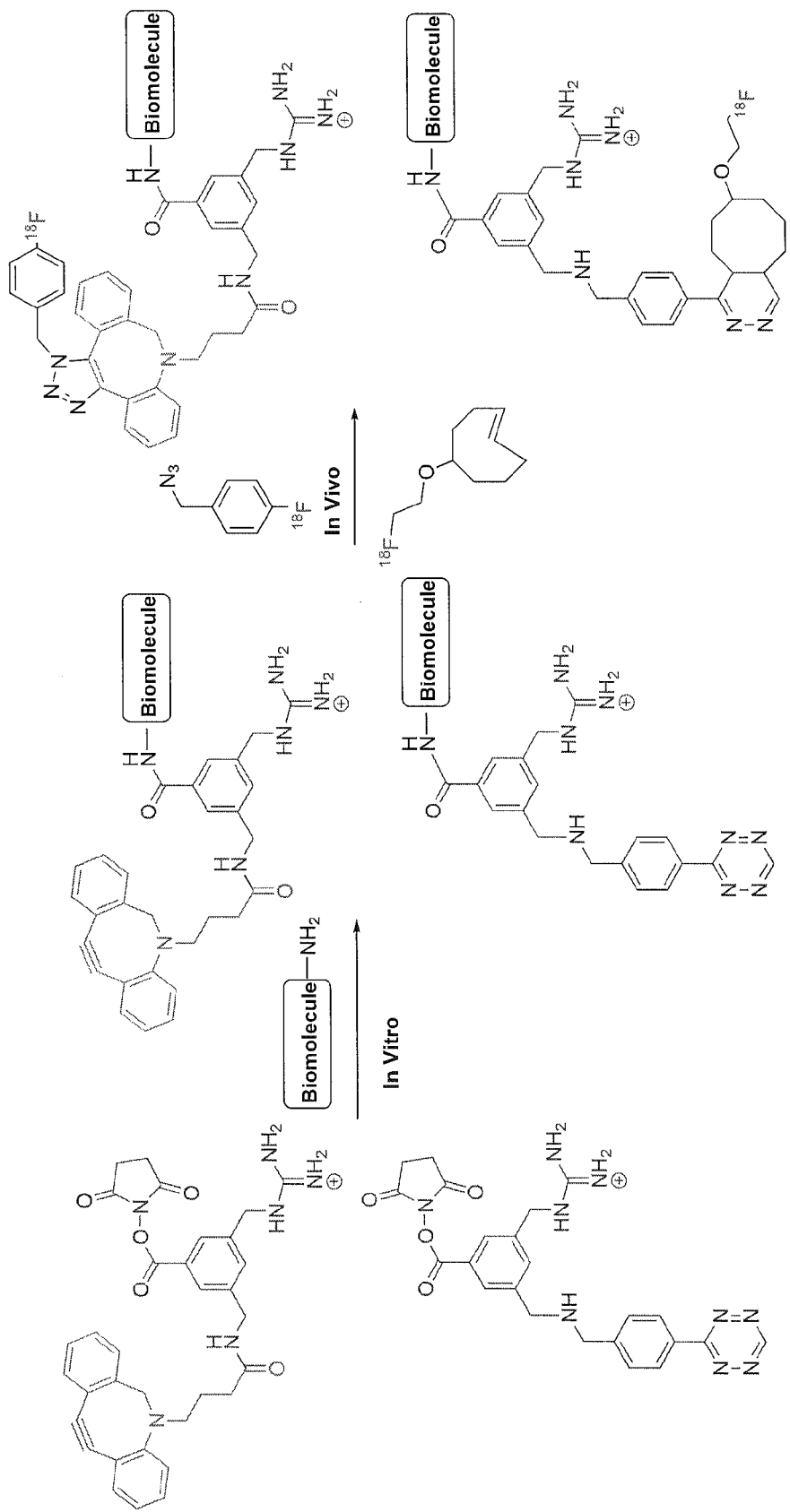
Figure 10. Examples of pretargeting via bioorthogonal chemistry. Top: dibenzocyclooctyne-azide strain-promoted click reaction. Bottom: Tetrazine-trans-cyclooctene inverse Diels Alder cycloaddition.

PROSTHETIC COMPOUNDS FOR LABELING INTERNALIZING BIOMOLECULES

CROSS-REFERENCE TO RELATED APPLICATIONS

This application is a U.S. National Stage application under 35 U.S.C. §371 of International Application PCT/US2014/036615 (published as WO 2014/179715 A1), filed May 2, 2014, which claims priority to U.S. provisional application No. 61/818,722, filed May 2, 2013. Benefit of the filing date of each of these prior applications is hereby claimed. Each of these prior applications is hereby incorporated by reference in its entirety.

FIELD OF THE INVENTION

The present invention relates to compounds useful for radiolabeling, preferably with fluorine-18 ($^{18}F$), of biomolecules such as antibodies, antibody fragments, and peptides. The compounds can effectively retain radioactivity that becomes internalized within cells, rendering such compounds useful in cancer diagnosis and treatment.

DESCRIPTION OF RELATED ART

A number of monoclonal antibodies (mAbs), mAb fragments and peptides have been labeled with different radionuclides and then used in the detection and treatment of cancers. Many of the most clinically relevant molecular targets such as HER2, epidermal growth factor receptor (EGFR), and the tumor-specific mutant EGFRvIII, rapidly internalize into tumor cells. This is a major problem from a labeling perspective because when radiolabeled biomolecules bind to the tumor associated receptors or antigens, they are transported into the cell, get taken up in endosomes/lysosomes where they are degraded rapidly. The difficulty is that these radioactive degradation products can then rapidly escape from the tumor cells. As a result, the sufficient radioactivity is no longer present within tumor cells to allow imaging or treatment of the tumor.

As an example, consider labeling a mAb reactive with EGFRvIII with radioiodine, in which the standard labeling method used is direct electrophilic substitution. In such cases, as a result of extensive internalization, the radioactivity retained within the tumor is low after receptor binding and subsequent proteolytic degradation. This is due to the rapid washout of the principal catabolite iodotyrosine. To circumvent this problem, "residualizing agents" have been developed which attempt to trap the radioactivity inside the tumor cell after the labeled mAb is internalized. Such residualizing agents for radioiodine include N-succinimidyl 4-guanidinomethyl-3-iodobenzoate (SGMIB); N$^\epsilon$-(3-iodobenzoyl)-Lys$^5$-N$^\alpha$-maleimido-Gly$^1$-Geeek, wherein e and k represent residues of D-glutamic acid and D-lysine, respectively, otherwise known as N$^2$-(2-(2,5-dioxo-2,5-dihydro-1H-pyrrol-1-yl)acetyl)-D-glutamyl-D-glutamyl-D-glutamyl-N'-(3-iodobenzoyl)-D-lysine or IB-MalGeeek; and 2,2',2''-(10-(2-((6-(3-(((2,5-dioxopyrrolidin-1-yl)oxy)carbonyl)-5-iodobenzamido)hexyl)amino)-2-oxoethyl)-1,4,7,10-tetraazacyclododecane-1,4,7-triyl)triacetic acid (SIB-DOTA) (see FIG. 1). Compared with the directly labeled biomolecule, considerable enhancement in tumor retention of radioactivity has been seen when the same biomolecule was labeled with one of these prosthetic groups (see FIG. 2).

Positron emission tomography (PET), a state-of-the art imaging technology, is very sensitive and has excellent quantitative capability. The most widely available positron-emitting radionuclide throughout the world is fluorine-18, which has a half-life of 110 min. To combine the advantages of this imaging technique with the targeting properties of internalizing molecules, it is necessary to develop residualizing agents with which these biomolecules can be labeled with fluorine-18.

SUMMARY OF THE INVENTION

The present invention is associated with the discovery of prosthetic compounds that are effective for radiolabeling biomolecules with $^{18}F$. Representative biomolecules include antibodies (e.g., monoclonal antibodies (mAbs) and nanobodies (single domain antibodies; sdAbs)), antibody fragments, and peptides that may have an affinity for particular types of cells, such as cancer cells. The prosthetic compounds effectively address the art-recognized difficulties associated with the retention of radioactivity within the targeted cells, due to internalization of the biomolecule, followed by proteolytic degradation. Due to differences in the radiochemistry between radioiodine and fluorine-18, as well as significant differences in the synthesis of compounds bearing these radionuclides, novel structures and labeling approaches are required for the effective delivery of fluorine-18 to cells, as well as the effective retention of radioactivity within the cells following internalization of the appropriate radiolabeled biomolecule.

Representative prosthetic compounds comprise, consist of, or consist essentially of (i) a succinimidyloxycarbonyl (i.e., succinimidyl ester) moiety, (ii) an $^{18}F$-bearing moiety, and (iii) a charged moiety, i.e., a moiety that is charged under the physiological conditions of the internal cell environment. Without being bound by theory, it is believed that catabolites containing the charged moiety (e.g., bearing a positive or a negative charge), resulting from receptor-mediated internalization of the prosthetic compound-conjugated biomolecule and subsequent lysosomal degradation of the receptor-biomolecule complex, effectively trap radioactivity within the target cells due to the inability of charged, radiolabeled catabolites to cross lysosomal and cell membranes.

One embodiment of the invention relates to a composition. The composition may be useful for internally labeling a cell, or otherwise for trapping radioactivity within a cell. The composition comprises a biomolecule and an $^{18}F$-labeled prosthetic compound. The biomolecule is any moiety that specifically binds to a cell surface antigen or receptor and is internalized by the cell. The biomolecule may be selected from the group consisting of an antibody, a nanobody, a fragment of an antibody, and a synthetic polypeptide.

Another embodiment of the invention relates to a method for coupling an $^{18}F$-labeled prosthetic compound to a biomolecule, wherein the $^{18}F$-labeled prosthetic compound and the biomolecule are as described herein. The biomolecule may be coupled directly or otherwise coupled through an oligopeptide intermediate. Representative proteolysis-resistant oligopeptides, which may serve as suitable intermediates are described in U.S. Pat. No. 6,998,106, and the disclosure of these oligopeptides is hereby incorporated by reference. Using the coupling or conjugation methods described herein, including the optional removal of non-radiolabeled side products that otherwise have the capability to react with and consume the biomolecule, conjugation efficiencies can exceed 10%, with representative conjugation efficiencies being generally in the range from about 10% to about 60%, and often from about 20% to about 40%, measured as the percentage of the starting $^{18}$F-labeled prosthetic compound that is coupled to the biomolecule (e.g., nanobody) used in the conjugation reaction.

Another embodiment of the invention relates to a method for synthesizing an $^{18}$F-labeled prosthetic compound as described above, wherein the synthesis proceeds through the formation of an azide or triazolyl-ring containing intermediate, as discussed in greater detail below. Using the synthesis methods described herein, based on the formation of the disclosed $^{18}$F-labeled prosthetic compounds, decay-corrected radiochemical yields can exceed 5%, with representative decay-corrected radiochemical yields being generally in the range from about 10% to about 50%, typically from about 10% to about 30%, and often from about 10% to about 20%, measured as the percentage of the starting $^{18}$F radioactivity, added to the synthesis reaction mixture, which is successfully incorporated into $^{18}$F-labeled prosthetic compound. The percentage is corrected (i.e., revised upward) to account for the amount of radioactive decay of $^{18}$F during the time between radioactivity measurements (e.g., in millicurie, mCi) taken before and after the synthesis reaction.

Another embodiment of the invention relates to a method of incorporating a label into a cell. The method comprises the step of contacting the cell with the composition described above, whereby the label is internalized by the cell.

Still another embodiment of the invention relates to a method of locating tumor cells in a mammal. The method comprises the steps of introducing a diagnostically effective amount of the above composition into the body of a mammal which comprises tumor cells, scanning the body with a PET detector or a scintillation detector, and generating an image depicting the tumor cells in the body of the mammal.

Yet another embodiment of the invention relates to a method of radiotherapy. The method comprises the step of introducing a therapeutically effective amount of the above composition into the body of a mammal comprising a tumor, whereby growth of the tumor is diminished.

These and other embodiments and aspects relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying drawings.

FIG. 1 depicts structures of residualizing agents for radioiodine.

FIG. 2 depicts the effectiveness of the residualizing agents of FIG. 1 in retaining radioactivity within tumor cells.

FIG. 3 depicts a synthetic scheme for preparing an $^{18}$F-labeled prosthetic compound.

FIG. 4 depicts, in the synthetic scheme of FIG. 3, potential side reactions, leading to the formation of an unwanted byproduct.

FIG. 5 depicts an approach to react or scavenge out the byproduct depicted in FIG. 4, whereby the reaction product is easily separable from the $^{18}$F-labeled prosthetic compound.

FIG. 6 depicts the intracellularly trapped radioactivity over a 4-hour time period, resulting from the internalization of nanobody biomolecules coupled to $^{18}$F-labeled prosthetic compound as described herein.

FIGS. 7, 8, and 9 depict synthetic schemes for preparing other $^{18}$F-labeled prosthetic compounds.

FIG. 10 depicts an alternative radiolabeling approach based on pretargeting, using a prosthetic compound having a reporter group that bears an azide or alkyne moiety and is reactive with an $^{18}$F radiolabeled probe.

DETAILED DESCRIPTION

Aspects of the invention relate to prosthetic compounds, as described herein, for labeling biomolecules with $^{18}$F. Other aspects of the invention relate to radiolabeled biomolecules and methods of their use in locating and treating tumors. These and other aspects of the invention are apparent from the description of various embodiments described below.

Representative $^{18}$F-labeled prosthetic compounds according to the invention have the general structure of Formula I:

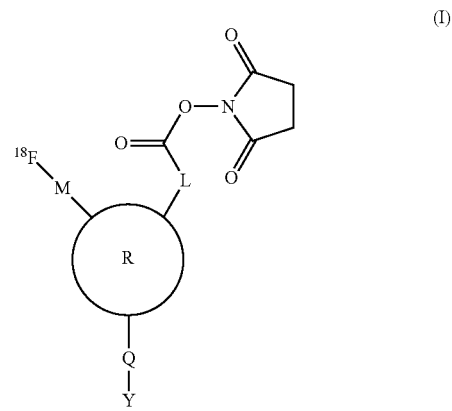

wherein Y is a charged group, and L, M, and Q are a succinimidyloxycarbonyl linker, an $^{18}$F linker, and a charged group linker, respectively. Thus, the moieties (i) succinimidyloxycarbonyl-L-, (ii) $^{18}$F-M-, and (iii) Y-Q- constitute the succinimidyloxycarbonyl moiety, the $^{18}$F-bearing moiety, and the charged moiety, respectively. These moieties are each bonded to a core structure R. According to some embodiments, R may be a saturated, unsaturated (e.g., aromatic), or partially unsaturated ring structure comprising a hydrocarbon ring, or two or more fused hydrocarbon rings, having from 3 to 12 carbon atoms, one or more of which carbon atoms of one or more of the rings may be replaced by a heteroatom such as NH, O, or S (in which case a hydrocarbon ring having such replacement may be referred to as a heterocyclic ring), and/or one or more of which carbon atoms may be optionally substituted. A representative core structure R is a benzene ring. Bivalent, intermediate linkers L, M, and Q may be varied in length and/or may incorporate substitutents to impart desired charge, electronic, geometric (e.g., spacing), biological (e.g., proteolysis resistance), and/or steric effects of the prosthetic compound, thereby tailoring the compound for interaction with a specific biomolecule, target cell, and/or cellular environment.

Linkers may also be selected to facilitate bonding of the respective moieties to the core structure. For example, as discussed in greater detail below with respect to a preferred synthesis pathway for the prosthetic compound, a representative $^{18}$F linker, M, is a bifunctional alkyl chain (e.g., —CH$_2$—, —C$_2$H$_4$—, —C$_3$H$_6$—, etc.) having from 1 to 10 carbon atoms, in which one carbon atom may be substituted with a cyclic (hydrocarbon ring) radical or heterocyclic (heterocyclic ring) radical. Representative heterocyclic radicals have at least one nitrogen atom in the heterocyclic ring. Specific examples of such heterocyclic radicals are therefore diazinyl, diazolyl, triazinyl, triazolyl, tetrazinyl, and tetrazolyl radicals. These and other heterocyclic radicals, or otherwise cyclic radicals, may optionally be fused to a another cyclic or heterocyclic radical, or otherwise fused to a another cyclic or heterocyclic radical that is itself part of a fused ring system (e.g., a triazolyl radical may be fused to an 8-membered cyclic or heterocyclic radical that is itself fused to two 6-membred cyclic rings, as in the case of the triazolyl radical (or other nitrogen atom-substituted heterocyclic hydrocarbon radical) being fused to a dibenzoazocanyl radical). Therefore, linkers containing three or more fused rings, such as hydrocarbon rings, heterocyclic rings, and combinations of these rings, are possible. A representative charged group linker, Q, is a bivalent alkyl chain having from 1 to 10 carbon atoms. Generally, L, M, and/or Q may be bivalent alkyl radicals, having from 1 to 20 carbon atoms, wherein one or more carbon atoms may be substituted with and/or replaced by a heteroatom such as NH, O, or S, or otherwise may be substituted with or replaced by another alkyl radical (e.g., resulting in the formation of a branched alkyl radical) having from 1 to 8 carbon atoms that may be linear, branched, or cyclic. For example, one carbon atom of an alkyl radical may be substituted to provide a carbonyl (C=O) group, and an adjacent carbon atom replaced by NH, thereby resulting in a peptide linkage —(C=O)—NH—. Representative linkers L, M, and Q therefore include divalent alkyl radicals having one or more of such peptide linkages, —NH— linkages, —(C=O)— linkages, and/or cyclic —C$_6$H$_4$— linkages, including combinations of any two, three, or four of such linkages, incorporated into the alkyl chain. In addition, in the case of bivalent alkyl radicals for L, M, and/or Q, a carbon-carbon double bond and/or a carbon-carbon triple bond may be formed between one or more pairs of adjacent carbon atoms, to provide bivalent, unsaturated (e.g., olefinic) alkyl radicals.

According to some embodiments, linkers L, M, and/or Q may simply be a bond, meaning that (i) the succinimidyloxycarbonyl of the succinimidyloxycarbonyl moiety, (ii) $^{18}$F of the $^{18}$F-bearing moiety, and/or (iii) the charged group (Y) of the charged moiety may be bonded directly to the core structure R. For example, according to some embodiments linker L is a bond, resulting in a subgenus of compounds having the general structure of Formula II:

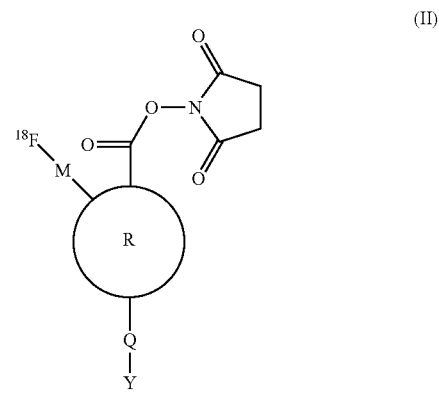

(II)

Preferably, charged group Y is a guanidino group or other group that exhibits a positive charge under the physiological conditions to which the prosthetic compounds are exposed. A positively charged group Y advantageously retains $^{18}$F within the cell targeted in a diagnostic (e.g., imaging) or treatment method.

Specific examples of prosthetic compounds are N-succinimidyl, 3-((4-(4-fluorobutyl)-1H-1,2,3-triazol-1-yl)methyl)-5-(guanidinomethyl)benzoate, including its $^{18}$F derivative, as shown below.

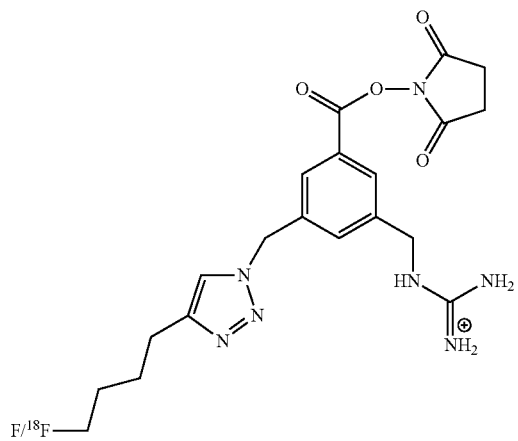

Removal of the radionuclide linker, M, in the above compound results in the direct bonding of the radionuclide, $^{18}$F, to the core structure, R, which in this compound is a benzene ring. The resulting prosthetic compound of the invention is N-succinimidyl, 5-fluoro-3-(guanidinomethyl) benzoate, having the structure

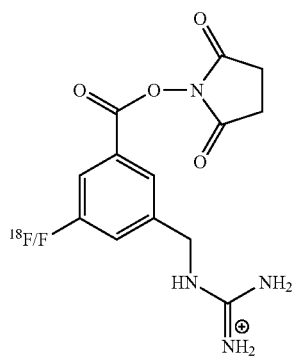

Various positional isomers of the above compounds may also be utilized for biomolecule labeling. One example is N-succinimidyl, 3-fluoro-4-(guanidinomethyl)benzoate, having the following structure that is also within the scope of the prosthetic compounds of the invention:

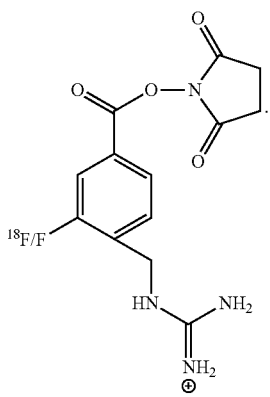

Radiolabeling can occur by first coupling a non-$^{18}$F-labeled prosthetic compound to a biomolecule as described herein, wherein the non-$^{18}$F-labeled prosthetic compound corresponds to the $^{18}$F-labeled prosthetic compounds as described above, but has a reporter group (S) in place of the radionuclide $^{18}$F. The reporter group is reactive with an $^{18}$F radiolabeled probe, allowing radiolabeling to occur after coupling between the prosthetic compound and the biomolecule. Further representative prosthetic compounds (e.g., for use in in vivo radiolabeling with $^{18}$F) therefore include those having the general structures of Formulas Ia and IIa below:

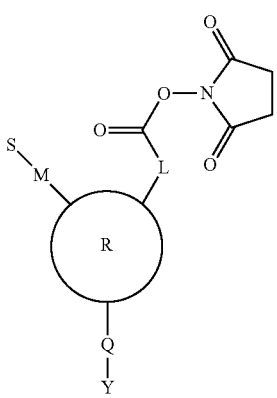

(Ia)

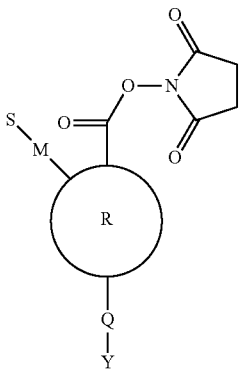

(IIa)

wherein linkers L, M (in this case a reporter group linker), and Q are as defined above. Reporter group S allows for covalent bonding of $^{18}$F, subsequent to coupling between prosthetic compounds having these structural formulas (Ia and IIa) and their respective biomolecules. Representative reporter groups can bear moieties such as an azide, alkyne (terminal or part of a strained homocyclic or heterocyclic ring), trans-cyclooctene, norbornene, tetrazine, etc. Thus, representative reporter groups can bear an alkyne moiety as part of a cyclic or heterocyclic radical or fused ring system radical. FIG. 10 depicts representative radiolabeling methods based on "pretargeting" and using prosthetic compounds as described above, having reporter groups that bear alkyne or tetrazine moieties that are reactive with complementary $^{18}$F radiolabeled probes. Pretargeting, for example, can involve administering, to a mammal, a biomolecule that is coupled to a prosthetic compound having structural formula Ia or IIa above, in which charged group Y is a guanidino group and reporter group S is a dibenzocyclooctynyl radical or heterocyclic derivative thereof that nevertheless retains the carbon-carbon triple bond in the ring or fused ring system. Otherwise, reporter group S may, for example, be a tetrazinyl radical according to one of the specific embodiments shown in FIG. 10. Subsequently, an $^{18}$F radiolabeled probe that is reactive with reporter group S (e.g., is bioorthogonal to a reporter group bearing an alkyne or tetrazine moiety) may be administered to the mammal (e.g., human) such that the probe reacts with the reporter group on the biomolecule-coupled prosthetic compound after this compound is already localized on a tumor of the mammal. In this manner, the tumor may be radiolabeled in vivo.

All of the above mentioned methods can likewise be used for deriving residualizing agents based on 1B-MalGeeek and SIB-DOTA as well.

Biomolecules

Representative biomolecules that may be coupled to $^{18}$F-labeled prosthetic compounds described above include any molecule that specifically binds to a cell surface receptor or antigen. Representative cell surface antigens or receptors include those that are internalized by the cell. Biomolecules can be internalized by the cell over seconds, minutes, hours, or days. Preferred biomolecules are internalized rapidly, i.e., most of the biomolecule is internalized after minutes to hours. A biomolecule is considered to bind specifically when it binds with an affinity constant ($K_A$) of $10^6$ M$^{-1}$ or more, preferably $10^8$ M$^{-1}$ or more. Cell surface receptors or antigens can be internalized either with or without a bound biomolecule. An example of an internalizing receptor is the epidermal growth factor receptor (EGFR), which is internalized by the process of receptor-mediated endocytosis. Other examples of internalizing receptors, which can serve as targets for biomolecules, include HER2, and the tumor-specific mutant EGFRvIII. Antigens or receptors which are internalized by the cell can eventually become localized within endosomes or lysosomes.

A biomolecule can be an antibody, a fragment of an antibody, or a synthetic peptide that binds specifically to a cell surface antigen or receptor. Antibodies include monoclonal antibodies (mAbs) and nanobodies (or single-domain antibodies, sdAbs). In a preferred embodiment the biomolecule is an internalizing antibody. Any antibody that specifically binds to a cell surface antigen and is internalized by the cell is an internalizing antibody. The antibody can be an immunoglobulin of any class, i.e., IgG, IgA, IgD, IgE, or IgM, and can be obtained by immunization of a mammal such as a mouse, rat, rabbit, goat, sheep, primate, human or other suitable species, including those of the camelidae family. The antibody can be polyclonal, i.e., obtained from the serum of an animal immunized with a cell surface antigen or fragment thereof. The antibody can also be monoclonal, i.e., formed by immunization of a mammal using the cell surface ligand or antigen or a fragment thereof, fusion of lymph or spleen cells from the immunized mammal with a myeloma cell line, and isolation of specific hybridoma clone, as is known in the art. The antibody can also be a recombinant antibody, e.g., a chimeric or interspecies antibody produced by recombinant DNA methods. A preferred internalizing antibody is a humanized antibody comprising human immunoglobulin constant regions together with murine variable regions which possess specificity for binding to a cell surface antigen (see, e.g., Reist et al., 1997). If a fragment of an antibody is used, the fragment should be capable of specific binding to a cell surface antigen. The fragment can comprise, for example, at least a portion of an immunoglobulin light chain variable region and at least a portion of an immunoglobulin heavy chain variable region. A biomolecule can also be a synthetic polypeptide which specifically binds to a cell surface antigen. For example, the biomolecule can be a synthetic polypeptide comprising at least a portion of an immunoglobulin light chain variable region and at least a portion of an immunoglobulin heavy chain variable region, as described in U.S. Pat. No. 5,260,203 or as otherwise known in the art.

Internalizing mAbs

Many of the known molecular targets for labeled mAbs are internalizing antigens and receptors. B-cell lymphoma (Press et al., 1994; Hansen et al., 1996), T-cell leukemia (Geissler et al., 1991) and neuroblastoma cells (Novak-Hofer et al., 1994) all possess antigens that are internalized rapidly. Internalizing receptors have been used to target mAbs to tumors. These include wild-type epidermal growth factor receptor (EGFR; gliomas and squamous cell carcinoma; Brady et al., 1992; Baselga et al., 1994), the p185 c-erbB-2 oncogene product (breast and ovarian carcinomas; De Santes et al. 1992; Xu et al., 1997), and the transferrin receptor (gliomas and other tumors; Laske et al., 1997). Indeed, it has been suggested that internalization can occur with virtually any mAb that binds to a cell-surface antigen (Mattes et al., 1994; Sharkey et al., 1997a).

An advantage of mAb internalization for radioimmunotherapy is the potential for increasing the radiation absorbed dose delivered to the cell nucleus. Dosimetry calculations suggest that even with the multicellular range β-emitter $^{131}$I, shifting the site of decay from the cell membrane to cytoplasmic vesicles could increase the dose received by the cell nucleus by a factor of two (Daghighian et al., 1996). On the other hand, a disadvantage of mAb internalization is that this event exposes the mAb to additional catabolic processes that can result in the release of radioactivity from the tumor cell.

EGFRvIII—A Tumor-Specific Target

Over-expression of wild-type EGFR receptor occurs in a variety of cancers. However, EGFR is also present on many normal tissues, detracting from its merit for tumor targeting. In addition to causing overexpression, oncogenic transformation can also lead to re-arrangements of EGFR genes, including some which are characterized by deletion mutations in the receptor's extracellular domain (Wong et al., 1992). One of these, EGFRvIII, has an in-frame deletion of 801 base pairs, resulting in the removal of NH$_2$-terminal amino acids 6 to 273 and the generation of a novel glycine residue at the fusion point. This produces a 145 kDa mutant receptor, compared with 170 kDa for wild-type EGFR (Humphrey et al., 1990). Expression of EGFRvIII has been reported on the majority of gliomas, medulloblastomas, breast and ovarian carcinomas, as well as 16% of small cell lung carcinomas (Garcia de Palazzo et al., 1993; Moscatello et al., 1995; Wikstrand et al., 1995). EGFRvIII has not been found on normal tissues, including those expressing wild-type EGFR. Because EGFRvIII is only expressed in cells undergoing malignant transformation, this molecule appears to be truly tumor specific and thus of great value for diagnostic and therapeutic applications. Quantitative flow cytometry of biopsies from glioma patients has revealed an average of $3 \times 10^5$ to $7 \times 10^5$ EGFRvIII receptors per cell (Wikstrand et al., 1997), a level that should be more than sufficient for tumor targeting. Antibodies that are specific for EGFRvIII were developed using a 14-mer peptide corresponding to the fusion junction as the immunogen (Humphrey et al., 1990; Wikstrand et al., 1995). Several mAbs, including L8A4, Y10, and H10, have affinity constants ($K_A$) for binding to EGFRvIII-positive HC2 20 d2 cells of between $1.3 \times 10^9$ and $2.5 \times 10^9$ M$^{-1}$ after radioiodination (Reist et al., 1995).

The murine anti-EGFRvIII mAb L8A4 IgG1 was developed using protocols involving immunization of BALB/c mice with a synthetic peptide representing the unique EGFRvIII sequence as well as EGFRvIII-positive HC2 20 d2 cells (Wikstrand et al., 1995). This mAb specifically precipitates mutant 145-kDa EGFRvIII but not wild-type 170 kDa EGFR, and is internalized into EGFRvIII-expressing cells within 5 min of binding to the receptor (Reist et al., 1995). The affinity constant for murine L8A4 binding to the neoepitope of EGFRvIII, determined by surface plasmon resonance, is $2.0 +/- 1.0 \times 10^9$ M$^{-1}$ (Reist et al., 1997). Single chain F$_v$ (scF$_v$) constructs based on the L8A4 variable region can also be used instead of the whole L8A4 antibody. An scF$_v$ monomer was labeled with N-succimidinyl [*I]iodopyridine carboxylate ([*I]SIPC) and found to have a K$_A$ of 1.5×10$^8$ M$^{-1}$ and an immunoreactive fraction of 65-80%. Multivalent constructs have been created by varying the length of the linker between the V$_L$ and V$_H$ domains; with a 5 amino acid linker, a dimer has been generated with a K$_A$ of 5.5×10$^9$ M$^{-1}$ measured by surface plasmon resonance.

Chimeric Antibodies

Repeated doses of murine antibodies in humans as required for optimal therapeutic efficacy lead to the development of human anti-mouse antibody responses (Tjandra et al., 1990) which may cause allergic reactions or inhibit targeting of the murine antibody to the tumor. This problem can be addressed by producing human/murine recombinant antibodies (also called humanized antibodies), which contain the tumor-specific murine variable regions linked to a human immunoglobulin constant region. A chimeric recombinant version of L8A4 (chL8A4) was produced, which possesses the anti-EGFRvIII specificity of the murine L8A4 antibody together with the constant domains of human IgG$_2$ (for details of the generation of chL8A4 see Reist et al., 1997, and references therein). Human IgG$_2$ has a low affinity for F$_c$ receptors; the use of its constant regions thus minimizes non-specific uptake. After labeling with [$^{125}$I]- or [$^{131}$I]-SIPC, the tumor uptake properties of ch L8A4 were similar to those of murine L8A4. However, normal tissue uptake was increased by 2-fold at 72-120 hours (Reist et al., 1997), suggesting some differences in processing and normal tissue uptake compared to the murine antibody. Further details on the production of chimeric antibodies by recombination methods can be found in Hoogenboom et al., 1996, U.S. Pat. No. 5,565,332.

The biomolecule can be coupled to the $^{18}$F-labeled prosthetic compound, for example, by covalent bonding to a free amino, thiol, or carboxyl group of the biomolecule, or otherwise to a free amino, thiol, or carboxyl group of an intermediate oligopeptide, referenced above. Generally, an N-succinimidyl group of a prosthetic compound is reactive with an amino group of a biomolecule or intermediate.

Detection of radioactivity from the $^{18}$F-labeled prosthetic compound can be performed by standard radiological methods, including, for example, scanning the body with a scintillation detector (radioscintigraphy) and positron emission tomography (PET) (see, e.g., Bradwell et al., 1985). For in vivo use the $^{18}$F-labeled prosthetic compound, coupled to a biomolecule, should be given in either diagnostically or therapeutically acceptable amounts. A therapeutically acceptable amount is an amount which, when given in one or more dosages, produces the desired therapeutic effect, e.g., shrinkage of a tumor, with a level of toxicity acceptable for clinical treatment. Such an administered amount will cause sufficient radiation to absorb within tumor cells so as to damage these cells, for example by disrupting their DNA. Such an administered amount preferably should cause minimal damage to neighboring healthy cells.

Both the dose of a particular composition and the means of administering the composition can be determined based on specific qualities of the composition, the condition, age, and weight of the patient, the progression of the particular disease being treated, and other relevant factors. If the composition contains antibodies, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg. A diagnostically acceptable amount is an amount which permits detection of radioactivity from the $^{18}$F-labeled prosthetic compound as required for diagnosis, with a level of toxicity acceptable for diagnosis.

EXAMPLES

The following examples are set forth as representative of the present invention. These examples are not to be construed as limiting the scope of the invention as these and other equivalent embodiments will be apparent in view of the present disclosure and appended claims.

Synthesis of N-succinimidyl 3-((4-(4-fluorobutyl)-1H-1,2,3-triazol-1-yl)methyl)5-(guanidinomethyl) benzoate (SFBTMGMB)

In this molecule for fluorine-18 labeling, two important design elements, the active N-hydroxysuccinimidyl ester and the guanidine function, were incorporated. Unlike radioiodine, which can be easily introduced by the electrophilic substitution of tin moieties, the approach for labeling with fluorine-18 is not straightforward. In particular, introducing $^{18}$F on the aromatic ring using standard radiosynthetic methods is not practical with a molecule analogous to N-succinimidyl 4-guanidinomethyl-3-iodobenzoate (SGMIB). Normally, for $^{18}$F-labeling, it would be possible to displace a leaving group such as tosylate or mesylate on an alkyl side chain with [$^{18}$F]fluoride. However, due to the susceptibility of the N-hydroxysuccinimide ester, present in the desired molecule, for displacement under conditions specifically required for fluorination, alternatives to conventional labeling chemistry have now been investigated for providing the desired, $^{18}$F-labeled prosthetic compounds at acceptable radiochemical yields.

Aspects of the invention therefore relate the discovery that a click chemistry approach can be used in the effective synthesis of the $^{18}$F-labeled prosthetic compounds described herein. Specific radiolabeling chemistry involves a copper-catalyzed cycloaddition reaction between an azide moiety on the parent compound and a terminal alkyne moiety of [$^{18}$F]fluoroalkyne, in order to convert the azide group to a triazole ring, substituted with [$^{18}$F]fluoroalkyl. Conversely, it is possible to place the alkyne and azide moieties on the parent compound and $^{18}$F-containing compound, respectively. In an initial approach, a molecule containing an azide group, in addition to the active ester and the guanidine function (compound 7; FIG. 3), was designed as the precursor compound/molecule. The guanidine function advantageously creates the positive charge necessary to trap the $^{18}$F-labeled degradation products inside cells after receptor-mediated internalization of biomolecules. A standard of SFBTMGMB was synthesized by the click reaction of this azide-containing precursor with fluorohexyne to give compound 8. Removal of the tert-butoxycarbonyl (Boc) protecting groups with TFA yielded SFBTMGMB. For the $^{18}$F-labeled derivative, the same azide precursor was clicked with [$^{18}$F]fluorohexyne, which in turn was generated from a corresponding tosylate precursor. Boc$_2$-[$^{18}$F]SFBTMGMB ([$^{18}$F] compound 8; FIG. 3) was prepared from wet [$^{18}$F] fluoride in two steps in 100-110 min with an average overall decay-corrected radiochemical yield of 12.0±3.6% (n=17). The Boc protecting groups were removed and the resultant [$^{18}$F]SFBTMGMB was coupled to an anti-HER2 nanobody.

Occasional loss in conjugation efficiency of [$^{18}$F]SFBTMGMB to a nanobody was attributed to the formation of an unlabeled side product that elutes in HPLC very closely to the desired, labeled product. Without being bound by theory, it is believed that this side product formed by the click reaction of starting azide (7, FIG. 3) with one of the potential side products in the initial $^{18}$F-labeling step (compound C, FIG. 4; see Seo et al. BULL. KOREAN CHEM. SOC. 2011, Vol. 32(1): 71-76). A standard of this putative side product (compound E, FIG. 4) was synthesized, and indeed it has the same retention (elution) time in HPLC as the observed side product. Since this product contains an N-succinimidyl ester function, it can compete with the nanobody (i.e., is reactive with the nanobody). Strategies therefore focused on (i) the removal of this side product during aqueous work up of the click reaction step or (ii) the alteration of the retention time in HPLC of the side product. According to one particular solution, a second click reaction was performed after the initial one, using an azide-bearing molecule containing a quaternary salt moiety (compound F, FIG. 5) to convert compound E to compound G, as shown in FIG. 5. Nanobody labeling was restored in most cases by conducting this second click reaction, followed by isolation of the reaction product. For example, in one embodiment, the second click reaction may be used to render the reaction product between the non-radiolabeled side product and a suitable scavenger compound more hydrophilic (e.g., by incorporating a charged group into the scavenger compound and reaction product, as shown in FIG. 5). In this manner, the reaction product may be separable by preferential extraction into an aqueous extraction medium. An anti-HER2 nanobody, 5F7 was labeled using [$^{18}$F]SFBTMGMB with a conjugation efficiency of 24.5±13.6% (n=15).

TCA precipitation (97.5±2.0%), SDS-PAGE (96.3±1.0%), and ITLC (98.6±2.0%) indicated that more than 95% of radioactivity was associated with the nanobody. Immunoreactivity of the labeled 5F7 was determined by Lindmo assay using magnetic beads coated with extracellular domain of HER2, and as control, those with bovine serum albumin. The labeled nanobody bound specifically to the HER-positive magnetic beads; immunoreactivity was 62-64%. A paired-label internalization assay was performed using HER2-expressing BT474M1 breast cancer cells. For this, 5F7 nanobody labeled using [$^{18}$F]SFBTMGMB and that using [$^{125}$I]SGM1B were incubated with the cells and the intracellularly trapped radioactivity was determined by a standard protocol. Importantly, over a 4-hour period, the intracellularly trapped radioactivity from nanobodies labeled by both methods was similar (FIG. 6).

Synthesis of Other Residualizing Agents for labeling Internalizing Biomolecules with Fluorine-18

As an extension of the above, the alkyne moiety can be placed on the aromatic ring, and the $^{18}$F on the fluoroalkyl azide. There are a number of copper-free, strain-promoted cycloaddition reactions that may be incorporated for labeling. The guanidine-containing molecule can be modified with such molecules for clicking with $^{18}$F-labeled complementary molecule. An example of this is shown in FIG. 7. Another way to label biomolecules is to first modify them by conjugating with a prosthetic group as described herein, but having, in place of the $^{18}$F-bearing moiety, an azide-, an alkyne-, or other bioorthogonal functional group bonded to the core structure R, optionally through a linker M (wherein R and M are as defined above). The click reaction can then be performed using the modified biomolecule with a suitable, $^{18}$F-labeled complementary molecule. Using the $^{18}$F-labeling chemistry described herein, it is also possible to synthesize an SGMIB analogue with fluorine instead of iodine in the molecule (FIG. 8). Fluorine-18 labeling by the silicon fluoride acceptor (SiFA) method is becoming common and the synthesis and application of [$^{18}$F]SiFB, a protein/peptide labeling agent analogous to [$^{18}$F]SFB (Vaidyanathan and Zalutsky, NATURE PROTOCOLS, 2006; 1: 1655-1661) has been described (Kostikov et al., NATURE PROTOCOLS, 2012; 7: 1956-1963; Kim et al., J. LABELLED COMPD. RADIOPHARM. 2013; 56: S157; Yasui et al., LABELLED COMPD. RADIOPHARM. 2013; 56: S158). A guanidine containing analogue of this compound can be synthesized in a single step from a suitable precursor (FIG. 9). A protein may be modified first with the precursor, as has been demonstrated for peptides, and then the protein may be labeled directly in a single step.

Overall, aspects of the invention are directed to the radiolabeling of biomolecules with $^{18}$F. In particular embodiments, radiolabeled monoclonal antibodies and peptides are used in the detection and treatment of cancer. Some of these biomolecules undergo extensive internalization after binding to the tumor associated receptor or antigen, which results in their rapid degradation. When these molecules are labeled using conventional methods, these radioactive degradation products escape from the tumor cell, and as a result of this, the radioactivity is no longer available to image the tumor or to treat it. To circumvent this problem, so-called residualizing agents have been developed that trap the radioactivity inside the target cell so it can be imaged or treated. Positron Emission Tomography (PET) is the state-of-the-art imaging technology that is now used routinely throughout the world for imaging cancer and other types of disease. Fluorine-18 is the most widely available and utilized radionuclide for PET imaging but no methods are available to label internalizing proteins or peptides with F-18 that will result in high trapping of the radioactivity in target cells after biomolecule internalization. The present invention addresses this problem, which should open the door for imaging internalizing biomolecules with F-18 and PET. Those having skill in the art, with the knowledge gained from the present disclosure, will recognize that various changes can be made in prosthetic compounds, $^{18}$F-labeled biomolecules, and synthesis methods described herein, without departing from the scope of the present invention.

The invention claimed is:

1. A prosthetic compound having the general structure of Formula I:

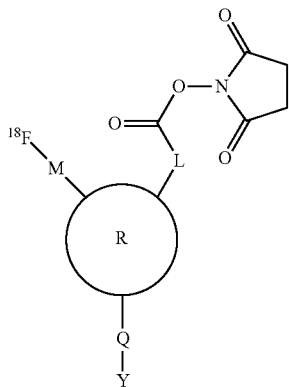

(I)

wherein Y represents a charged group, and L, M, and Q represent a succinimidyloxycarbonyl linker, an $^{18}$F linker, and a charged group linker, respectively, and wherein R represents a benzene ring.

2. The prosthetic compound of claim 1, wherein L, M, and Q independently represent a bond or a bivalent alkyl radical, having from 1 to 20 carbon atoms, wherein (i) one or more carbon atoms may be substituted with or replaced by a heteroatom, (ii) one or more carbon atoms may be substituted with or replaced by another alkyl radical having from 1 to 8 carbon atoms that may be linear, branched, or cyclic, and (iii) one or more pairs of adjacent carbon atoms may form a carbon-carbon double bond or a carbon-carbon triple bond.

3. The prosthetic compound of claim 1, wherein Y represents a guanidino group.

4. The prosthetic compound of claim 3, which is selected from the group consisting of the $^{18}$F derivative of N-succinimidyl,3-((4-(4-fluorobutyl)-1H-1,2,3-triazol-1-yl) methyl)-5-(guanidinomethyl)benzoate, the $^{18}$F derivative of N-succinimidyl, 5-fluoro-3-(guanidinomethyl)benzoate, and the $^{18}$F derivative of N-succinimidyl, 3-fluoro-4-(guanidinomethyl)benzoate.

5. A composition for internally labeling a cell, the composition comprising a biomolecule that is conjugated to the $^{18}$F-labeled prosthetic compound of claim 1.

6. The composition of claim 5, wherein the biomolecule is selected from the group consisting of an antibody, a fragment of an antibody, and a synthetic polypeptide.

7. The composition of claim 5, wherein the $^{18}$F-labeled prosthetic compound and biomolecule are conjugated directly or conjugated through an oligopeptide intermediate.

8. The prosthetic compound of claim 2, wherein L represents a bond.

9. The prosthetic compound of claim 8, wherein Y represents a guanidino group.

10. A prosthetic compound having the general structure of Formula I:

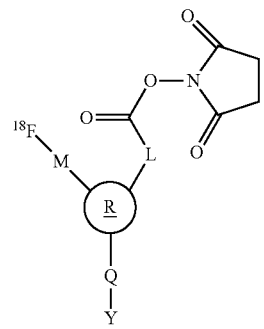

(I)

wherein R is a core structure; Y represents a charged group; and L, M, and Q represent a succinimidyloxycarbonyl linker, an $^{18}$F linker, and a charged group linker, respectively, and wherein M is a bivalent alkyl radical, having from 1 to 20 carbon atoms, wherein (i) one or more carbon atoms may be substituted with or replaced by a heteroatom, (ii) one or more carbon atoms may be substituted with or replaced by another alkyl radical having from 1 to 8 carbon atoms that may be linear, branched, or cyclic, and (iii) one or more pairs of adjacent carbon atoms may form a carbon-carbon double bond or a carbon-carbon triple bond.

11. The prosthetic compound of claim 10, wherein R represents a saturated, unsaturated, or partially unsaturated ring structure comprising a hydrocarbon ring, or two or more fused hydrocarbon rings, having from 3 to 12 carbon atoms, one or more of which carbon atoms of the ring structure may be optionally replaced by a heteroatom and one or more of which carbon atoms may be optionally substituted.

12. The prosthetic compound of claim 10, wherein R represents a benzene ring.

13. The prosthetic compound of claim 10, wherein L and Q independently represent a bond or a bivalent alkyl radical, having from 1 to 20 carbon atoms, wherein (i) one or more carbon atoms may be substituted with or replaced by a heteroatom, (ii) one or more carbon atoms may be substituted with or replaced by another alkyl radical having from 1 to 8 carbon atoms that may be linear, branched, or cyclic, and (iii) one or more pairs of adjacent carbon atoms may form a carbon-carbon double bond or a carbon-carbon triple bond.

14. The prosthetic compound of claim 10, wherein Y represents a guanidino group.

15. A prosthetic compound having the general structure of Formula I:

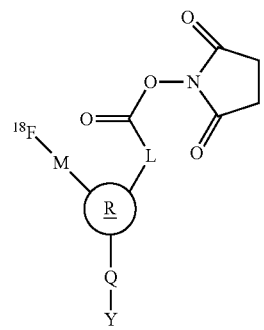

(I)

wherein R is a core structure; Y represents a charged group; and L, M, and Q represent a succinimidyloxycarbonyl linker, an $^{18}$F linker, and a charged group linker, respectively, and wherein Q is a bivalent alkyl radical, having from 1 to 20 carbon atoms, wherein (i) one or more carbon atoms may be substituted with or replaced by a heteroatom, (ii) one or more carbon atoms may be substituted with or replaced by another alkyl radical having from 1 to 8 carbon atoms that may be linear, branched, or cyclic, and (iii) one or more pairs of adjacent carbon atoms may form a carbon-carbon double bond or a carbon-carbon triple bond.

16. The prosthetic compound of claim 15, wherein R represents a saturated, unsaturated, or partially unsaturated ring structure comprising a hydrocarbon ring, or two or more fused hydrocarbon rings, having from 3 to 12 carbon atoms, one or more of which carbon atoms of the ring structure may be optionally replaced by a heteroatom and one or more of which carbon atoms may be optionally substituted.

17. The prosthetic compound of claim 15, wherein R represents a benzene ring.

18. The prosthetic compound of claim 15, wherein L and M independently represent a bond or a bivalent alkyl radical, having from 1 to 20 carbon atoms, wherein (i) one or more carbon atoms may be substituted with or replaced by a heteroatom, (ii) one or more carbon atoms may be substituted with or replaced by another alkyl radical having from 1 to 8 carbon atoms that may be linear, branched, or cyclic, and (iii) one or more pairs of adjacent carbon atoms may form a carbon-carbon double bond or a carbon-carbon triple bond.

19. The prosthetic compound of claim 15, wherein Y represents a guanidino group.

* * * * *